US006543302B1

(12) United States Patent
Pratt

(10) Patent No.: US 6,543,302 B1
(45) Date of Patent: Apr. 8, 2003

(54) MULTIPLE CHECK VALVE BAILER

(76) Inventor: David W. Pratt, 13512 Feather Sound Cir., Clearwater, FL (US) 33760

( * ) Notice: Subject to any disclaimer, the term of this patent is extended or adjusted under 35 U.S.C. 154(b) by 0 days.

(21) Appl. No.: 09/682,747

(22) Filed: Oct. 12, 2001

(51) Int. Cl.$^7$ ................................................. G01N 1/12
(52) U.S. Cl. ................................ 73/864.63; 73/863.71; 294/68.22
(58) Field of Search ......................... 73/864.63, 864.65, 73/864.66, 864.67, 863.71; 294/68.22, 68.25

(56) References Cited

U.S. PATENT DOCUMENTS

| | | | |
|---|---|---|---|
| 1,388,602 A | | 8/1921 | Rotteleur |
| 2,298,627 A | * | 10/1942 | Proudman et al. ........ 73/864.63 |
| 3,055,764 A | * | 9/1962 | Pryor et al. .......... 73/864.63 X |
| 3,455,904 A | * | 7/1969 | Hopkin ................ 73/864.63 X |
| 3,697,194 A | * | 10/1972 | Holmes ................... 166/109 X |
| 3,700,034 A | * | 10/1972 | Hutchison .................... 166/312 |
| 4,050,315 A | | 9/1977 | Markfelt |
| 4,185,579 A | | 1/1980 | Asher ......................... 114/211 |
| 4,305,279 A | * | 12/1981 | Ontek ..................... 73/864.63 |
| 4,512,441 A | | 4/1985 | Cooper ................... 184/105 B |
| 4,869,371 A | * | 9/1989 | Dickinson et al. .......... 206/577 |
| 5,139,089 A | * | 8/1992 | Wacker ....................... 166/311 |
| 5,507,194 A | | 4/1996 | Scavuzzo et al. ........ 73/864.63 |
| 5,753,831 A | * | 5/1998 | Mohs ....................... 73/864.63 |
| 5,755,559 A | | 5/1998 | Allington et al. ............. 417/53 |
| 6,276,220 B1 | * | 8/2001 | Varhol ................. 73/863.71 X |
| 6,390,123 B1 | * | 5/2002 | Pratt .................... 73/864.63 X |

\* cited by examiner

*Primary Examiner*—Thomas P. Noland
(74) *Attorney, Agent, or Firm*—Ronald E. Smith; Smith & Hopen, P.A.

(57) ABSTRACT

A bailer having multiple check valves to minimize leakage of sample fluid from the bailer. A primary check valve assembly including a ball and a seat are disposed at a lower end of the bailer. At least one auxiliary check valve assembly is positioned above the primary check valve assembly. When a first auxiliary check valve closes, the hydrostatic pressure applied to the primary check valve is reduced significantly and leakage through the primary check valve is reduced. When a second auxiliary check valve closes, the hydrostatic pressure applied to the first auxiliary check valve is reduced and the same benefits are obtained for the first auxiliary check valve. Particulate matter is collected in an annular trough formed in the primary check valve assembly and in pockets that form a part of each auxiliary check valve assembly.

13 Claims, 3 Drawing Sheets

MULTIPLE CHECK VALVE BAILER

BACKGROUND OF INVENTION

1. Field of the Invention

This invention relates, generally, to bailers. More particularly, it relates to a bailer having multiple check valves that reduce leakage of sample fluid from the bailer.

2. Description of the Prior Art

Bailers are used to sample liquid fluid from wells or other bodies of liquid fluid. The sample fluid retrieved using a bailer is tested and analyzed, usually by governmental authorities or their contractors, for impurities and contaminants. A typical bailer has a slender tubular-shaped main body and a check valve at the bottom end thereof. As an operator lowers the bailer into a liquid fluid using a cable or line attached to a top end of the bailer, the check valve opens and fluid enters the hollow interior of the bailer. The air displaced by the fluid exits the bailer from the open upper end thereof. The air flowing out of the top of the bailer prevents liquid fluid from entering the bailer through said open top.

When a filled bailer is removed from the body of liquid fluid, the check valve closes and secures the liquid sample within the bailer. The liquid sample is then distributed from the bailer to individual test containers for a battery of tests.

One of the problems confronting the bailer industry is leakage from a bailer via the check valve after a sample has been drawn. Leakage is undesirable for two primary reasons. First, the sample fluid captured within the bailer may be contain acids or other harmful constituents that may cause irritation if allowed to leak onto the skin of the operator taking the sample after the bailer is retrieved. Secondly, bailers are sized to hold a predetermined volume of liquid fluid that correlates with a particular testing protocol. Accordingly, excessive leakage of fluid from the bailer may necessitate a repeated sampling of the well or other body of fluid to accumulate the required sampling volume.

Leakage problems are compounded when the liquid fluid being sampled contains particulate matter such as sand. The sand or other particulate matter gets between the check valve seat and the check valve ball and prevents the ball from sealing the valve seat.

U.S. Pat. No. 5,507,194 to Scavuzzo et al. (hereinafter "Scavuzzo") describes a disposable bailer having an inlet means and an integrated check valve that includes a check ball that rests in a check seat at the lowermost end of the bailer as in many other prior art bailers. Scavuzzo discloses an improved design of the check valve whereby premature unseating of the check ball is prevented during emptying of the fluid sample into analysis containers. Specifically, the check valve is designed to not open until the bailer is near a horizontal position and mostly empty. An upper or outlet check valve means is designed to close when the bailer begins the ascent from the fluid body. Scavuzzo does not provide an improved means that reduces leakage of the fluid sample from the lower end of the bailer.

U.S. Pat. No. 4,050,315 to Markfelt describes a bailer that includes an upper spherical valve member activated when an operator imparts a sharp jerk on the lowering cable when the sampler has reached a desired depth. Once activated, the valve member lifts from an upper valve seat and allows fluid to fill the bailer with fluid from a desired depth. As the bailer fills, a lower floating ball contained within the body of the bailer rises to seat in a lower valve seat. The Markfelt invention thus enables the collection of a sample of liquid fluid from a predetermined depth, but the problem of leakage at the lowermost end of the bailer is not addressed.

Accordingly, there remains a need for a bailer design that does not leak.

However, in view of the prior art, considered as a whole at the time the present invention was made, it was not obvious to those of ordinary skill in the pertinent art how the needed bailer could be provided.

SUMMARY OF INVENTION

The long-standing but heretofore unfulfilled need for a bailer that does not leak is now provided by a new, useful, and nonobvious bailer. The novel bailer includes an elongate, tubular main body having a hollow interior, an upper end and a lower end. A primary check valve is slidingly received within the hollow interior at the lower end and at least one auxiliary check valve is slidingly received within the hollow interior in longitudinally spaced relation to the primary check valve. A barrier means is slidingly received within the hollow interior in longitudinally spaced relation to the at least one auxiliary check valve. The at least one auxiliary check valve is disposed between the primary check valve and the barrier means. The primary check valve and the at least one auxiliary check valve admit liquid fluid into the hollow interior of the bailer when the bailer is immersed within a body of liquid fluid. The primary and auxiliary check valves work in combination with one another to inhibit leakage of liquid fluid from the hollow interior.

At least some particulate matter in the liquid fluid contained within the hollow interior is collected in an annular trough formed at the lowermost end of the bailer. Additional particulate matter is collected by one or more pockets formed in the auxiliary valve assembly.

It is therefore understood that the primary object of this invention is to provide a bailer that doesn't leak.

A closely related is to provide a non-leaking bailer that is simple in construction, inexpensive to manufacture, reliable, and easy to assemble.

Another very important object is to provide a bailer that can be used effectively even when a liquid fluid being sampled contains particulate matter.

These and other important objects, advantages, and features of the invention will become clear as this description proceeds.

BRIEF DESCRIPTION OF DRAWINGS

For a fuller understanding of the nature and objects of the invention, reference should be made to the following detailed description, taken in connection with the accompanying drawings, in which.

DETAILED DESCRIPTION

Figure 1:
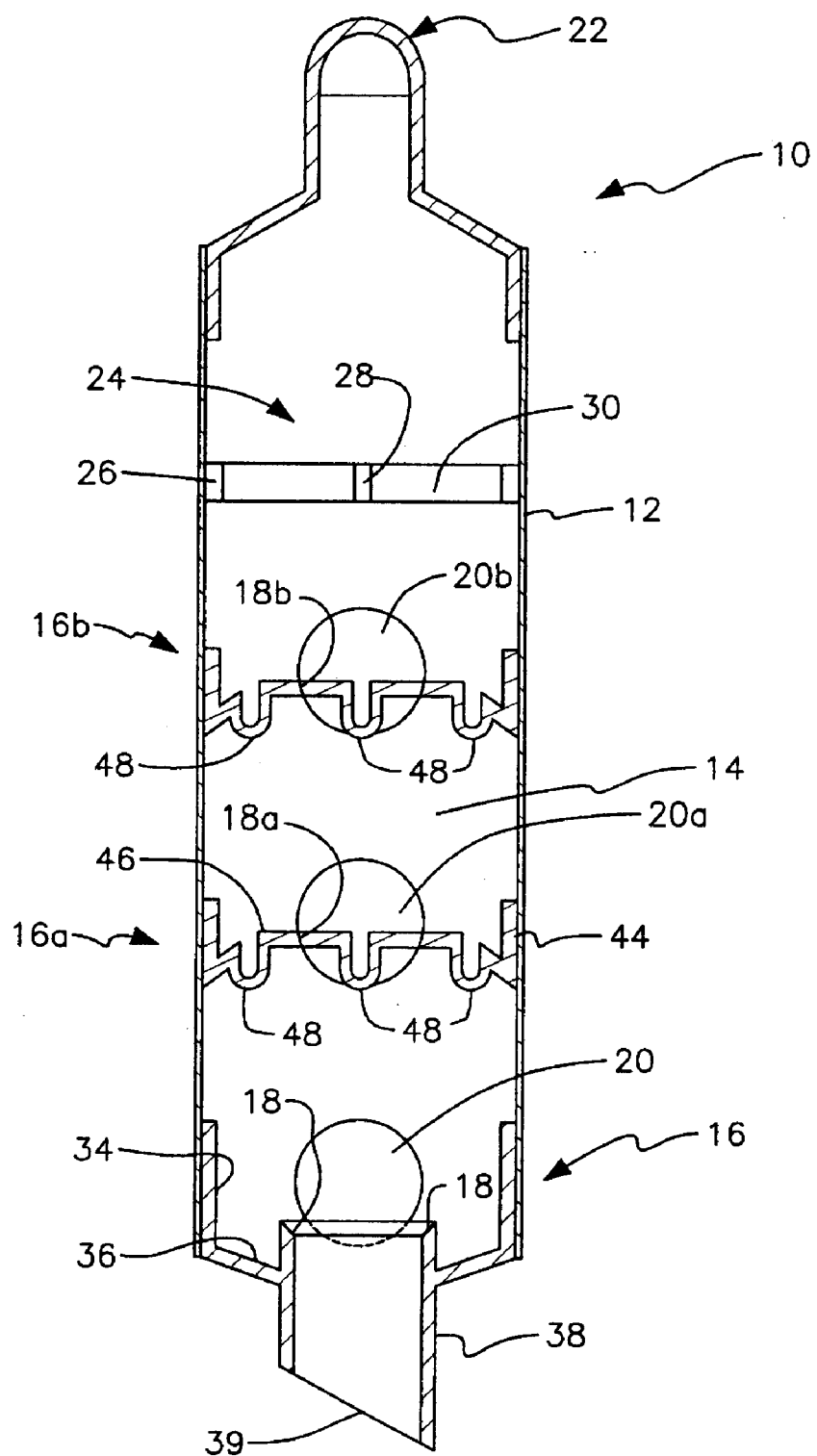
FIG. 1 is side elevational view of the novel bailer.

Referring now to FIG. 1, it will there be seen that the reference numeral 10 denotes an illustrative embodiment of the present invention as a whole.

It should be understood from the outset that the invention to be disclosed has utility with bailers of all types and sizes.

The bailer denoted 10 is merely one type of bailer and the invention is not restricted to bailers of the type depicted.

Illustrative bailer 10 includes tubular main body 12 that defines a hollow interior 14. It has a primary check valve assembly, denoted 16 as a whole, at its lowermost or leading end. In this illustrative example, two (2) auxiliary check valve assemblies 16a and 16b are positioned in hollow interior 14 of tubular main body 12 in vertically spaced relation to primary check valve 16. As will become clear as this description proceeds, any number of auxiliary check valve assemblies may be used, depending upon the requirements of individual applications. The use of at least one auxiliary check valve assembly is a critical aspect of this invention, i.e., whether the particular number of auxiliary check valve assemblies used in a particular application is one or two or more is not a critical aspect of this invention.

Primary check valve assembly 16 includes a primary check valve seat 18 and a primary check valve ball 20 that is seated in primary check valve seat 18 when bailer 10 is in a state of equilibrium. A state of equilibrium exists when the bailer is empty and not in use and shortly after a sample fluid has been collected within the hollow interior of the bailer and no further fluid is flowing into hollow interior 14. The qualification "shortly after" is used because it may take a few moments for primary check valve ball 20 to sink into primary check valve seat 18 after fluid has stopped flowing into said hollow interior. Primary check valve ball 16 rises and separates from primary check valve seat 18 when liquid fluid flows into hollow interior 14 of tubular main body 12. Primary check valve ball 20 returns to its seated position against said primary check valve seat 18 when said liquid fluid has ceased flowing into said hollow interior.

Two auxiliary check valves are depicted in FIG. 1 and denoted 16a, 16b, as aforesaid, but a different plurality of auxiliary check valves is within the scope of this invention. Each auxiliary check valve further increases the leak-inhibiting properties of the present invention. Auxiliary check valve seat 18a and auxiliary check valve ball 20a together comprise first auxiliary check valve 16a. Auxiliary check valve seat 18b and auxiliary check valve ball 20b together comprise second auxiliary check valve 16b.

The relatively short height or truncate longitudinal extent of auxiliary check valves 16a and 16b is an important feature of this invention because it enables the placing of a large number of auxiliary valves in the hollow interior 14 of tubular main body 12 if an application requires more than just one or two auxiliary check valves. Note in FIG. 1 that each auxiliary check valve assembly 16a, 16b has less longitudinal extent than primary check valve assembly 16.

Illustrative bailer 10 further includes closure means or cap 22 to which is secured a rope, not depicted, or other suitable means for lowering and lifting a bailer into and from a body of fluid. Cap 22 may be removed when collected fluid is poured from hollow interior 14 of the bailer, or it may be provided with an opening for that purpose so that it need not be removed. Cap 22 forms no part, per se, of this invention.

Weights (not shown) may be attached to the lower and upper end of tubular main body 12 to provide sufficient ballast to cause the bailer to submerge when lowered into a fluid body. Said weights form no part, per se, of this invention.

Figure 5:
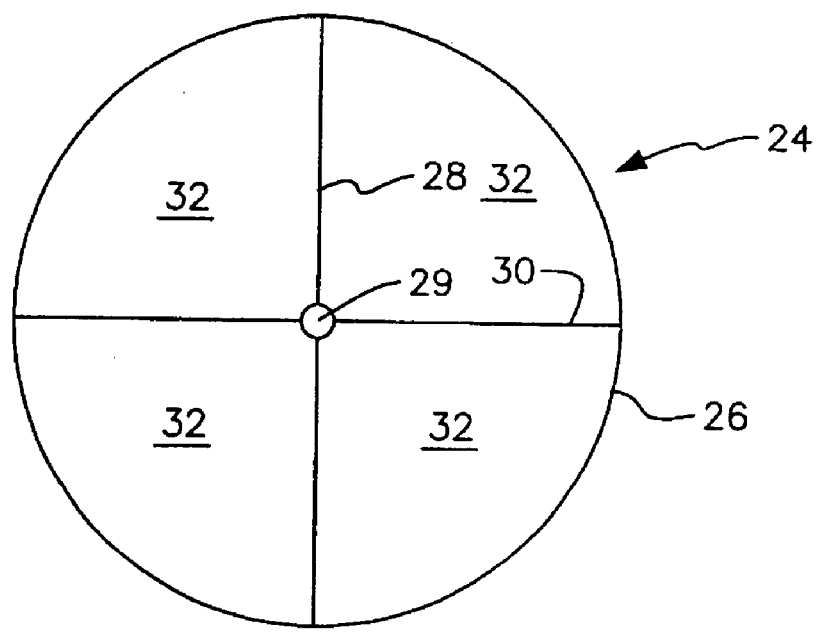
FIG. 5 is a top view of the barrier.

Barrier means 24 (FIGS. 1 and 5) is positioned above uppermost auxiliary check valve 16b and serves to restrain spherical check valve ball 20b as it rises with respect to auxiliary check valve seat 18b.

Barrier means 24 includes an annular wall 26 having a diameter slightly less than the interior diameter of tubular main body 12 so that said annular wall is slidingly positioned within hollow interior 14. Barrier means 24 may take many forms but in this particular embodiment it includes a pair of barrier arms 28, 30 that extend from hub 29 diametrically across hollow interior 14 of tubular main body 12. Each barrier arm has opposite ends secured to annular wall 26 in equidistantly and circumferentially spaced relation to one another so that said barrier arms are disposed at right angles to one another. Each of the spaces 32 collectively defined by said annular wall 26 and said barrier arms 28, 30 is smaller in breadth than auxiliary check valve ball 20b so that said auxiliary check valve ball cannot travel therethrough.

Barrier arms 28, 30 are narrow in construction to minimize resistance to fluid flow into hollow interior 14. Barrier means 24 need not be spaced far from auxiliary check valve assembly 16b. All that is needed is sufficient clearance for auxiliary check valve ball 20b to fully unseat from its check valve seat 18b when fluid flows into said hollow interior 14. A relatively short clearance is also desirable because it shortens the distance ball 20b must sink to become seated and hence the time required for such seating to take place after fluid stops flowing into hollow interior 14.

Figure 2:
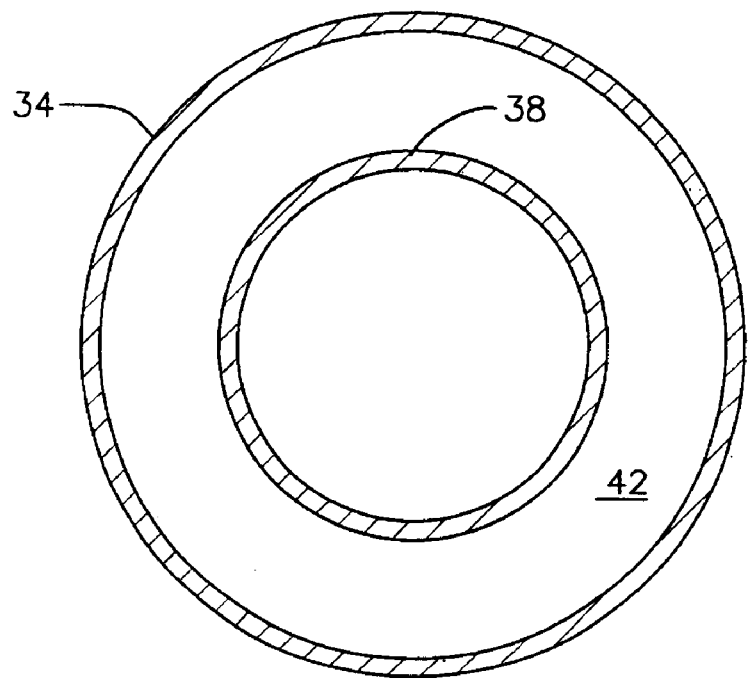
FIG. 2 is top view of the primary check valve.
Figure 3:
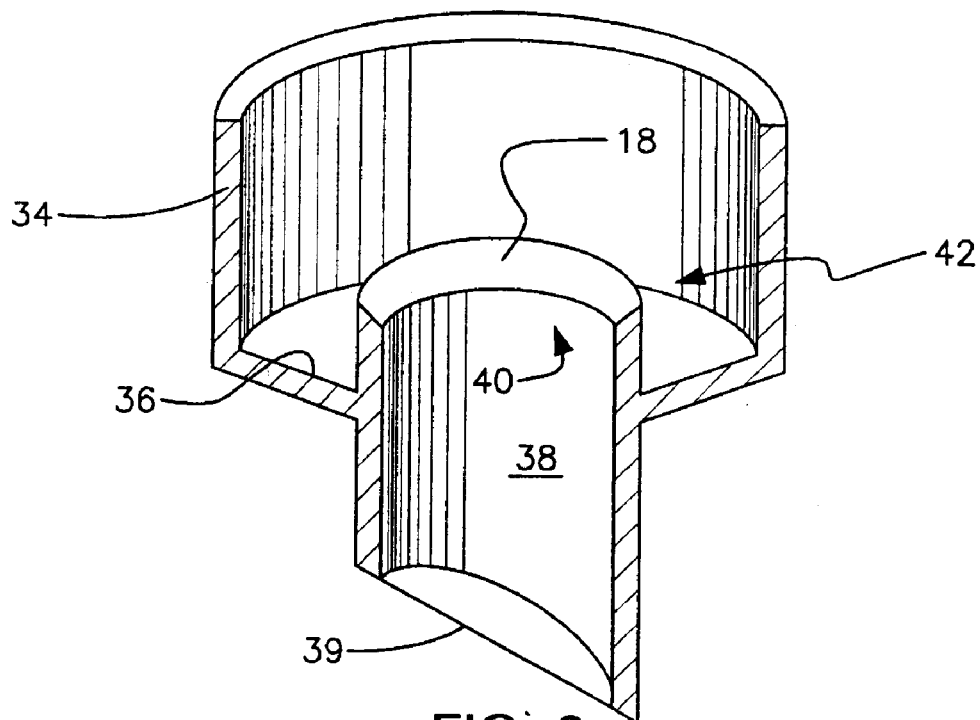
FIG. 3 is detailed side elevational view of the primary check valve.

Referring now with more particularity to the primary check valve assembly, it will be observed in FIGS. 2 and 3 that said assembly includes annular wall 34 having a diameter slightly less than that of tubular main body 12 so that said annular wall is slidingly positionable with hollow interior 14 of said tubular main body 12.

Bottom wall 36 is supported at its peripheral edges by annular wall 34 and in this particular embodiment said bottom wall is sloped downwardly as depicted.

Truncate tubular member 38 is disposed concentrically with respect to annular wall 34 and with respect to tubular main body 12 and is supported about its periphery by bottom wall 36. Note that the uppermost end 40 of truncate tubular member 38 forms primary check valve seat 16 and is positioned upwardly with respect to bottom wall 36. Accordingly, an annular trough 42 is formed for the collection of particulate matter. The particulate matter that collects within said trough 42 cannot interfere with the seating of primary check valve ball 20 upon its seat 18.

Bevel 39 is formed in the lowermost or leading end of truncate tubular member 38. Bevel 39 inhibits clogging of truncate tubular member 38 in those situations where a relatively thin layer of sediment has formed at the bottom of a well or other body of liquid fluid within which bailer 10 is used. In the absence of bevel 39, such a layer of sediment could potentially clog the entrance to truncate tubular member 38.

Figure 4:
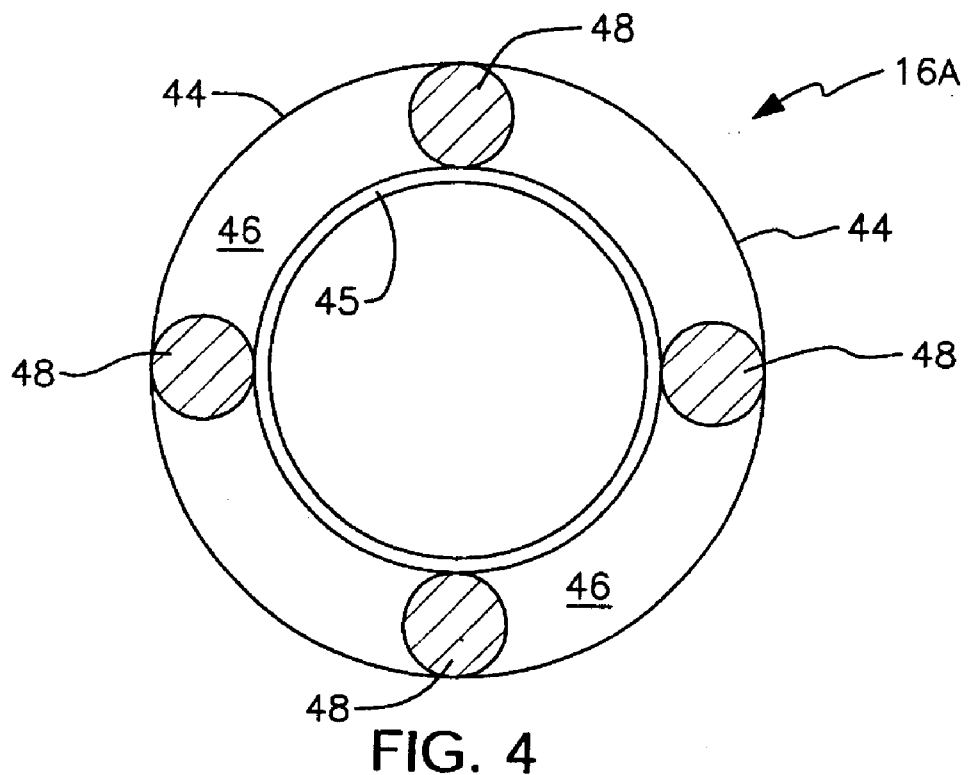
FIG. 4 is a top view of an auxiliary check valve.

As best understood in connection with FIGS. 1 and 4, auxiliary check valve means 16a includes annular wall 44 having a diameter slightly less than the interior diameter of tubular main body 12 so that it is slidingly positionable within hollow interior 14. Auxiliary check valve means 16a further includes bottom wall 46 having peripheral edges connected to annular wall 44. Bottom wall 46 is apertured as at 45 (FIG. 4) and said aperture 45 forms auxiliary check valve seat 18a for said auxiliary check valve ball 20a.

At least one pocket 48 is formed in bottom wall 46. Pocket 48 is adapted to collect particulate matter from the liquid fluid in hollow interior 14 so that particulate matter positioned within said at least one pocket can not interfere with seating of auxiliary check valve ball 20a on said auxiliary check valve seat 18a. In a preferred embodiment, as depicted in FIG. 4, said at least one pocket includes a plurality of pockets, collectively denoted 48, formed in bottom wall 46 in circumferentially spaced apart relation to one another.

The structure of auxiliary check valve 16b is the same as that of auxiliary check valve 16a.

Both primary check valve assembly 16 and the auxiliary check valve assemblies are thus unique in structure in view of their respective means for trapping particulates to reduce the chances that particulate matter will interfere with valve seating. Significantly, with one or more auxiliary check valves, the chances of a bailer leaking are very small.

When a fluid first flows upwardly into hollow interior 14, check valve balls 20, 20a, and 20b are unseated from their respective check valve seats 18, 18a, 18b in sequence with primary check valve ball 20 being unseated first. When fluid stops flowing into hollow interior 14, each ball settles into its associated seat.

In a conventional bailer, all of the hydrostatic pressure is applied to the lone check valve assembly at the lowermost end of the bailer. In the novel bailer, however, primary check valve assembly 16 is subjected only to the hydrostatic pressure of the fluid column below the first auxiliary check valve assembly 16a. Similarly, first auxiliary check valve assembly 16a bears only the hydrostatic pressure of the fluid column below the second auxiliary check valve assembly 16b and said second auxiliary check valve assembly 16b bears only the hydrostatic pressure of the fluid column above it. In this way, the hydrostatic fluid pressure applied to primary check valve assembly 16 is reduced by the sum of the hydrostatic pressures appearing on the first and second auxiliary check valve assemblies 16a, 16b, respectively. Thus, said primary check valve assembly is less likely to leak due to the decrease in hydrostatic pressure vis a vis conventional bailers. The same reduction in leakage applies as well to the second and third auxiliary check valve assemblies 16a, 16b, respectively.

Accordingly, none of the check valve assemblies is subjected to as much hydrostatic pressure as the check valves of the prior art. When that feature is coupled with the in-series arrangement of the check valves, the significant reduction in leakage achievable with this inventive structure becomes apparent.

The provision of particulate-trapping annular trough 42 in primary valve assembly 16 and pockets 48 in auxiliary valve assemblies 16a, 16b serves as further insurance against leakage.

The novel bailer thus represents the pinnacle of anti-leak bailers.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,
What is claimed is:

1. A bailer, comprising:

an elongate, tubular main body having a hollow interior;

said elongate, tubular main body having an upper end and a lower end;

a primary check valve slidingly received within said hollow interior at said lower end;

said primary check valve including a primary check valve seat and a primary check valve ball that is seated in said primary check valve seat when said bailer is in a state of equilibrium;

at least one auxiliary check valve slidingly received within said hollow interior of said tubular main body in longitudinally spaced relation to said primary check valve;

said at least one auxiliary check valve including at least one auxiliary check valve seat and at least one auxiliary check valve ball that is seated in said at least one auxiliary check valve seat when said bailer is in a state of equilibrium;

a barrier means slidingly received within said hollow interior of said main body in longitudinally spaced relation to said at least one auxiliary check valve; and said al least one auxiliary check valve being disposed between said primary check valve and said barrier means;

whereby said primary check valve and said at least one auxiliary check valve admit liquid fluid into said hollow interior of said bailer when said bailer in immersed within a body of liquid fluid;

whereby said primary check valve and said at least one auxiliary check valve work in combination with one another to inhibit leakage of liquid fluid from said hollow interior;

whereby said at least one auxiliary check valve functions as a barrier means when said primary check valve ball is unseated from said primary check valve seat as liquid fluid flows into said bailer; and whereby said barrier means functions as a barrier means when said at least one auxiliary check valve ball in unseated from said at least one auxiliary check valve seat as liquid fluid flows into said bailer.

2. The bailer of claim 1, wherein said at least one auxiliary check valve has a truncate longitudinal extent so that a plurality of said auxiliary check valves are positionable in spaced relation to one another within said hollow interior.

3. The bailer of claim 1, wherein said primary check valve further comprises:

an annular wall having a diameter slightly less than an internal diameter of said hollow interior so that said annular wall is adapted to be slidingly inserted into said hollow interior;

a truncate tubular member disposed concentrically with respect to said tubular main body and with respect to said annular wall;

said truncate tubular member having a first, uppermost end that forms said primary check valve seat;

said truncate tubular member having a diameter less than a diameter of said tubular main body and having a diameter less than said annular wall;

said primary check valve assembly further including an annular bottom wall that extends from a lowermost end of said annular wall and to said truncate tubular member, said annular bottom wall circumscribing said truncate tubular member and contacting said truncate tubular member at a predetermined annular juncture between said check valve seat and a lowermost end of said truncate tubular member;

whereby at least some particulate matter in the liquid fluid contained within said hollow interior is collected atop said annular bottom wall of said check valve assembly and therefore cannot flow through said truncate tubular member or settle atop said primary check valve seat to prevent said primary check valve ball from fully seating on said primary check valve seat.

4. The bailer of claim 3, further comprising:

a bevel formed in a lowermost end of said truncate tubular member, said lowermost end being a leading end of said truncate tubular member when said bailer is lowered into a body of liquid fluid;

whereby said bevel decreases a probability of particulate matter clogging said truncate tubular member when said bailer is lowered into a body of liquid fluid where particulate matter may form a sediment at the bottom thereof.

5. The bailer of claim 1, further comprising;

a closure means for closing said upper end of said bailer.

6. The bailer of claim 5, wherein said closure means includes an annular wall having a diameter slightly less than a diameter of said hollow interior so that said annular wall of said closure means is slidingly received within said hollow interior and so that said closure means may be removed to facilitate decanting of liquid fluid housed within said hollow interior after said bailer has been used.

7. The bailer of claim 5, wherein said closure means is adapted to be engaged by a means for lifting and lowering said bailer from and into, respectively, a body of liquid fluid.

8. The bailer of claim 1, wherein said at least one auxiliary check valve comprises:

an annular wall having a diameter slightly less than a diameter of said tubular main body so that said at least one check valve is slideably positionable within said hollow interior.

9. The bailer of claim 8, wherein said at least one auxiliary check valve further comprises:

a bottom wall having peripheral edges connected to said annular wall; and said bottom wall being apertured and said aperture forming an auxiliary valve seat for said auxiliary check valve ball.

10. The bailer of claim 9, further comprising:

at least one pocket formed in said bottom wall;

said pocket adapted to collect particulate matter in said liquid fluid so that particulate matter positioned within said pocket can not interfere with seating of said auxiliary check valve ball on said auxiliary check valve seat.

11. The bailer of claim 10, wherein said at least one pocket includes a plurality of pockets formed in said bottom wall in circumferentially spaced apart relation to one another.

12. A bailer, comprising:

an elongate, tubular main body having a hollow interior;

said elongate, tubular main body having an upper end and lower end;

a primary check valve slidingly received within said hollow interior at said lower end;

at least one auxiliary check valve slidingly received within said hollow interior of said tubular main body in longitudinally spaced relation to said primary check valve; and a barrier means slidingly received within said hollow interior of said main body in longitudinally spaced relation to said auxiliary check valve;

said at least one auxiliary check valve being disposed between said primary check valve and said barrier means;

a closure means for closing said upper end of said bailer;

said closure means including an annular wall having a diameter slightly less than a diameter of said hollow interior so that said annular wall of said closure means is slidingly received within said hollow interior and so that said closure means may be removed facilitate decanting of liquid fluid housed within said hollow interior after said bailer has been used;

whereby said primary check valve and said at least one auxiliary check valve admit liquid fluid into said hollow interior of said bailer when said bailer is immersed within a body of liquid fluid; and whereby said primary check valve and said at least one auxiliary check valve work in combination with one another to inhibit leakage of liquid fluid from said hollow interior.

13. A bailer, comprising:

an elongate, tubular main body having a hollow interior;

said elongate, tubular main body having an upper end and a lower end;

a primary check valve slidingly received within said hollow interior at said lower end;

at least on auxiliary check valve slidingly received within said hollow interior of said tubular main body in longitudinally spaced relation to said primary check valve; and a barrier means slidingly received within said hollow interior of said main body in longitudinally spaced relation to said auxiliary check valve;

said at least one auxiliary check valve being disposed between said primary check valve and said barrier means;

said auxiliary check valve including an auxiliary check valve seat and an auxiliary check valve ball that is seated in said auxiliary check valve seat when said bailer is in a state of equilibrium;

said barrier means serving as a barrier that limits upward travel of said auxiliary check valve ball when liquid fluid flows into said hollow interior;

said at least one auxiliary check valve including an annular wall having a diameter slightly less than a diameter of said tubular main body so that said at least one check valve is slideably positionable within said hollow interior;

said at least on auxiliary check valve further including a bottom wall having peripheral edges connected to said annular wall;

said bottom wall being apertured and said aperture forming an auxiliary valve seat for said auxiliary check valve ball;

at least one pocket formed in said bottom wall;

said pocket adapted to collect particulate matter in said liquid fluid so that particulate matter positioned within said pocket can not interfere with seating of said auxiliary check valve ball on said auxiliary check valve seat;

said at least one pocket including a plurality of pockets formed in said bottom wall in circumferentially spaced apart relation to one another;

whereby said primary check valve and said at least one auxiliary check valve admit liquid fluid into said hollow interior of said bailer when said bailer is immersed within a body of liquid fluid; and whereby said primary check valve and said at least one auxiliary check valve work in combination with one another to inhibit leakage of liquid fluid from said hollow interior.

* * * * *